(12) United States Patent
Fukazu et al.

(10) Patent No.: US 12,364,453 B2
(45) Date of Patent: Jul. 22, 2025

(54) RADIOGRAPHY CONTROL APPARATUS, IMAGE PROCESSING CONTROL METHOD AND STORAGE MEDIUM

(71) Applicant: Konica Minolta, Inc., Tokyo (JP)

(72) Inventors: Kosuke Fukazu, Hino (JP); Ryohei Ito, Hino (JP); Atsushi Taneda, Koganei (JP)

(73) Assignee: Konica Minolta, Inc., Tokyo (JP)

( * ) Notice: Subject to any disclaimer, the term of this patent is extended or adjusted under 35 U.S.C. 154(b) by 412 days.

(21) Appl. No.: 17/844,720

(22) Filed: Jun. 21, 2022

(65) Prior Publication Data
US 2022/0409163 A1    Dec. 29, 2022

(30) Foreign Application Priority Data
Jun. 25, 2021 (JP) ................. 2021-105988

(51) Int. Cl.
*A61B 6/00* (2024.01)
*A61B 6/42* (2024.01)
*H05G 1/44* (2006.01)

(52) U.S. Cl.
CPC ............ *A61B 6/542* (2013.01); *A61B 6/4233* (2013.01); *A61B 6/4291* (2013.01); *A61B 6/5294* (2013.01); *H05G 1/44* (2013.01)

(58) Field of Classification Search
CPC .................................................. A61B 6/5294
See application file for complete search history.

(56) References Cited

U.S. PATENT DOCUMENTS

2019/0223820 A1* 7/2019 Nemoto ............... A61B 6/5282
2020/0205769 A1* 7/2020 Kotian ................. A61B 6/542

FOREIGN PATENT DOCUMENTS

| JP | 2016-202219 A | 12/2016 |
| JP | 2017-225525 A | 12/2017 |
| JP | 2020-130691 A | 8/2020 |

OTHER PUBLICATIONS

Notice of Reasons for Refusal issued in corresponding Japanese Patent Application No. 2021-105988, dated Jan. 7, 2025, with translation (12 pages).

* cited by examiner

*Primary Examiner* — David P Porta
*Assistant Examiner* — Shun Lee
(74) *Attorney, Agent, or Firm* — Osha Bergman Watanabe & Burton LLP

(57) ABSTRACT

A radiography control apparatus includes a storage; a communicator that obtains irradiation information from an irradiation apparatus; and a hardware processor that: upon determining that the communicator obtains the irradiation information before a specific timing, executes image processing based on the irradiation information obtained from the communicator; and upon determining that the communicator does not obtain the irradiation information before the specific timing, executes the image processing based on information stored in advance in the storage.

8 Claims, 6 Drawing Sheets

| IMAGING REGION | TUBE VOLTAGE [kV] | TUBE CURRENT [mA] | TIME [ms] | EXPOSURE DOSE [mAs] | SID [cm] | GRID | FILTER | ... |
|---|---|---|---|---|---|---|---|---|
| HEAD, FRONT | 70 | 160 | 200 | 32 | 120 | + | Al | ... |
| CHEST, FRONT | 140 | 160 | 16 | 2.5 | 200 | + | Cu | ... |
| ABDOMEN, FRONT | 80 | 200 | 100 | 20 | 12 | + | Al+Cu | ... |
| ⋮ | ⋮ | ⋮ | ⋮ | ⋮ | ⋮ | ⋮ | ⋮ | ... |

221

RADIOGRAPHY CONTROL APPARATUS, IMAGE PROCESSING CONTROL METHOD AND STORAGE MEDIUM

CROSS-REFERENCE TO RELATED APPLICATIONS

The entire disclosure of Japanese Patent Application No. 2021-105988 filed on Jun. 25, 2021 is incorporated herein by reference.

BACKGROUND

Technical Field

The present disclosure relates to a radiography control apparatus, an image processing control method and a storage medium.

Description of Related Art

When radiographs of a subject are taken with radiation passing through the subject, the radiation is scattered in the subject according to the thickness of the subject, and scattered radiation is generated accordingly. This scattered radiation generates low-contrast radiographs.

In order to prevent the scattered radiation from affecting radiographs obtained by imaging, scattered radiation correction is performed on the radiographs. (Refer to, for example, JP 2016-202219 A and JP 2017-225525 A.).

As disclosed in JP 2016-202219 A and JP 2017-225525 A, scattered radiation correction uses irradiation information (imaging distance (SID: source to image distance), exposure dose (product of tube current and time), tube voltage, tube current, irradiation time, material of target and filter of radiation source, type of imaging stand, radiation field size, grid information, type of radiation detector, etc. at the time of imaging) as processing parameters. In a conventional radiography control apparatus, for example, irradiation conditions (imaging distance, exposure dose, tube voltage, tube current, irradiation time, material of target and filter of radiation source, type of imaging stand, radiation field size, grid information, type of radiation detector, etc.) for each imaging region are stored in advance in a storage as fixed information, and at the time of imaging, the fixed information for the imaging region or the like is read from the storage and set in an irradiation apparatus as irradiation conditions, and then imaging is performed. However, depending on the physique or the like of an examinee, it is possible that an irradiation condition(s) is changed to be different from that of the fixed information at an irradiation apparatus and radiography is performed. Since a conventional radiography control apparatus uses fixed information as processing parameters in scattered radiation correction, if an irradiation condition is changed at an irradiation apparatus and imaging is performed, the radiography control apparatus cannot perform scattered radiation correction accurately and needs to perform it again (i.e., reprocessing), which is troublesome. In the case where an irradiation condition is changed at an irradiation apparatus and imaging is performed, it is conceivable that an operator inputs the irradiation information accordingly and scattered radiation correction is performed. However, it is troublesome and may cause incorrect input.

Meanwhile, irradiation apparatuses that send, after exposure, the irradiation information to a radiography control apparatus(es) require different lengths of time to send the irradiation information to the radiography control apparatus. Hence, if a radiography control apparatus always waits to perform scattered radiation correction until it receives the irradiation information, timing at which the radiography control apparatus performs scattered radiation correction may be delayed, which results in requirement of a long time to display an image.

Such troublesomeness and delay arise in not only scattered radiation correction but also any image processing that is performed by using the irradiation information.

SUMMARY

Advantages provided by one or more embodiments of the present disclosure include not causing delay in displaying an image, not giving an operator trouble of performing reprocessing or inputting the irradiation information, and improving accuracy of image processing.

According to a first aspect of the present disclosure, there is provided a radiography control apparatus including:
an obtaining unit (i.e., communicator) that obtains irradiation information from an irradiation apparatus; and
a hardware processor that performs image processing based on the irradiation information obtained from the obtaining unit,
wherein the hardware processor:
in response to (upon determining that) the obtaining unit obtaining (obtains) the irradiation information before a specific timing, performs the image processing based on the irradiation information obtained from the obtaining unit; and
in response to (upon determining that) the obtaining unit not obtaining (does not obtain) the irradiation information before the specific timing, performs the image processing based on information stored in advance in the radiography control apparatus.

According to a second aspect of the present disclosure, there is provided an image processing control method including:
obtaining irradiation information from an irradiation apparatus; and
performing image processing based on the obtained irradiation information,
wherein the performing includes:
in response to obtaining the irradiation information before a specific timing (upon determining that the irradiation information is obtained before a specific timing), performing the image processing based on the irradiation information; and
in response to not obtaining the irradiation information before the specific timing (upon determining that the irradiation information is not obtained before the specific timing), performing the image processing based on information stored in advance in a storage.

According to a third aspect of the present disclosure, there is provided a non-transitory computer-readable storage medium storing a program that causes a computer to:
obtain irradiation information from an irradiation apparatus; and
perform image processing based on the obtained irradiation information,
wherein the program causes the computer to:
in response to obtaining the irradiation information before a specific timing (upon determining that the irradiation information is obtained before a specific timing), perform the image processing based on the irradiation information; and in response to not obtaining the irradiation information before the specific timing (upon determining that the irradiation information is not obtained before the specific timing), perform the image processing based on information stored in advance in a storage.

BRIEF DESCRIPTION OF THE DRAWINGS

The advantages and features provided by one or more embodiments of the present disclosure will become more fully understood from the detailed description given hereinbelow and the appended drawings that are given by way of illustration only, and thus are not intended as a definition of the limits of the present disclosure, wherein.

DETAILED DESCRIPTION OF EMBODIMENTS

Hereinafter, embodiments of the present disclosure will be described in detail with reference to the drawings. However, the scope of the present invention is not limited to the embodiments or illustrated examples.

<1. Outline of Radiographic System>

First, an outline of a radiographic system (hereinafter "system 100") according to one or more embodiments will be described.

Figure 1:
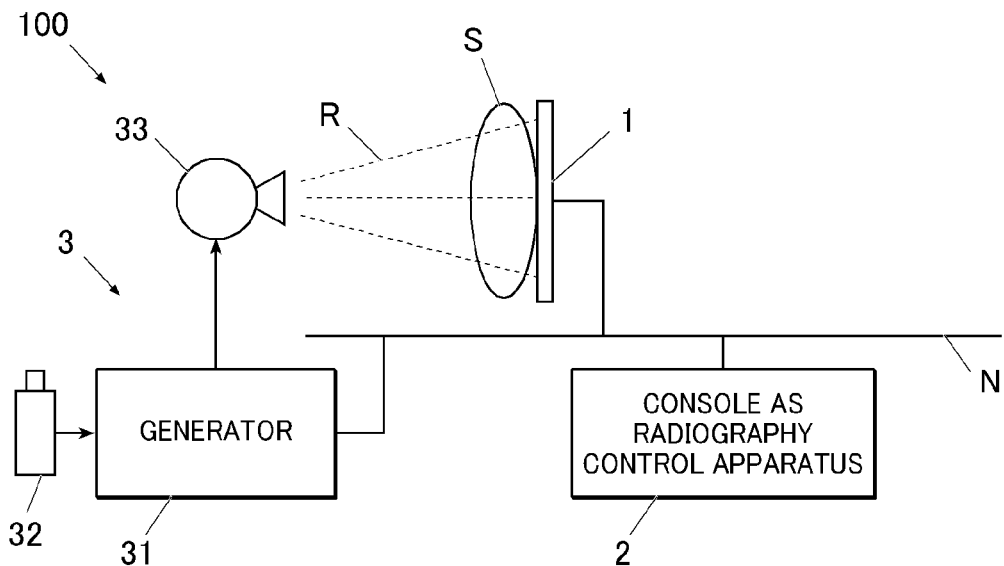
FIG. 1 is a block diagram showing an example of a radiographic system according to one or more embodiments of the present disclosure.

FIG. 1 is a block diagram showing an example of the system 100.

As shown in FIG. 1, the system 100 includes a radiation detector (hereinafter "detector 1"), a console 2 and an irradiation apparatus (hereinafter "irradiation apparatus 3").

These apparatuses 1 to 3 can communicate with one another, for example, via a communication network N (local area network (LAN), wide area network (WAN), Internet, etc.).

The system 100 is capable of communicating with a hospital information system (HIS), a radiology information system (RIS), a picture archiving and communication system (PACS), an analysis apparatus and so forth, all of which are not shown.

[1-1. Irradiation Apparatus]

The irradiation apparatus 3 performs irradiation.

The irradiation apparatus 3 includes a generator 31, an irradiation instructing switch 32 and a radiation source 33.

When receiving irradiation conditions for irradiation with radiation R (tube voltage, tube current, irradiation time, exposure dose, imaging distance (SID, distance from the radiation source 33 to the detector 1), grid information, material of target and filter of radiation source, type of imaging stand (e.g., for upright position or for decubitus position), radiation field size, type of detector, etc.) from the console 2, the generator 31 sets the received irradiation conditions as irradiation conditions to be used for radiography (imaging).

The generator 31 may be connected to an imaging stand (imaging stand for upright position, imaging stand for decubitus position, etc.) that holds the detector 1. In this case, on the basis of the type of imaging stand, the generator 31 moves the radiation source 33 to the front of the imaging stand to be used for imaging, or issues a warning if the detector 1 to be used is not mounted on the imaging stand.

The generator 31 is connected to a not-shown console panel, and when receiving a change made to an irradiation condition from this console panel, changes the setting of the irradiation condition in accordance with a value received/input. When the irradiation instructing switch 32 is operated, the generator 31 applies voltage suitable for the set irradiation conditions to the radiation source 33 (tube) and flows current suitable for the set irradiation conditions to the radiation source 33.

When the generator 31 applies the voltage and flows the current to the radiation source 33, the radiation source 33 generates and emits a dose of radiation R (e.g., X-rays) corresponding to the applied voltage and the flowed current in a mode suitable for the applied voltage and the flowed current.

[1-2. Radiation Detector]

Although not shown, the detector 1 includes a sensor substrate, a scanning circuit, a reading circuit, a controller and a communication unit. On the sensor substrate, pixels provided with radiation detecting elements and switching elements are arranged two-dimensionally (in a matrix). The radiation detecting elements generate electric charges corresponding to the dose of received radiation R. The switching elements accumulate and release the electric charges. The scanning circuit turns on and off each switching element. The reading circuit reads the amounts of the electric charges released from the respective pixels as signal values. The controller generates a radiograph from the signal values read by the reading circuit. The communication unit sends data of radiographs generated, various signals and so forth to the outside, and receives various pieces/types of information and various signals therefrom.

The detector 1 generates a radiograph corresponding to the dose of radiation R irradiated therewith, by accumulating and releasing electric charges and reading these as signal values in sync with being irradiated with the radiation R by the irradiation apparatus 3.

The detector 1 is not limited to a flat panel detector (FPD), but may be a CR cassette having a photo stimulable phosphor plate therein.

[1-3. Console]

The console 2 serves as a radiography control apparatus and is configured by a PC, a dedicated apparatus or the like.

The console 2 sets, on the basis of examination order information received from a not-shown HIS, RIS or the like, irradiation conditions in the irradiation apparatus 3 and image reading conditions in the detector 1. Further, the console 2 performs image processing including scattered radiation correction on radiographs sent from the detector 1 and displays the processed radiographs.

Details of the console 2 will be described below.

<2. Details of Console>

Next, details of the console 2 included in the system 100 will be described.

Figure 2:
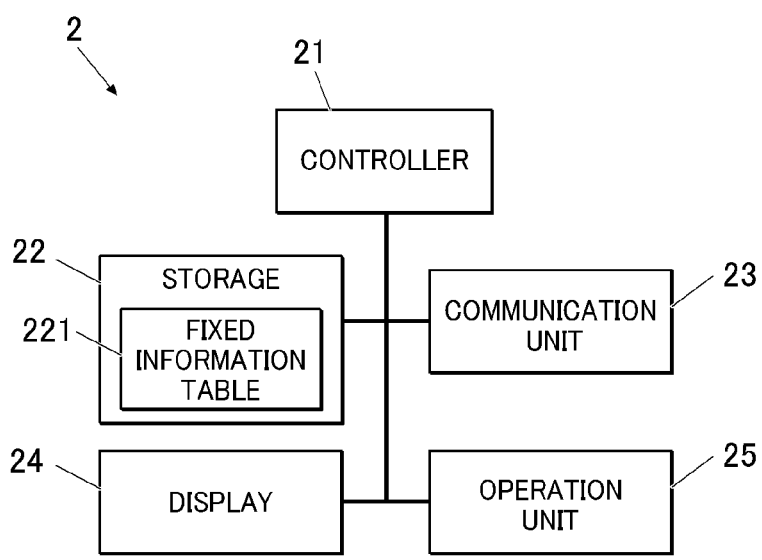
FIG. 2 is a block diagram showing a functional configuration of a console included in the radiographic system shown in FIG. 1.

FIG. 2 is a block diagram of the console 2.

[2.1 Specific Configuration of Console]

As shown in FIG. 2, the console 2 includes a controller 21 (hardware processor), a storage 22, a communication unit 23 (communicator or obtaining unit), a display 24 and an operation unit (user interface) 25.

These components 21 to 25 are electrically connected to one another by a bus or the like.

The controller 21 includes a CPU (Central Processing Unit) and a RAM (Random Access Memory). The CPU of the controller 21 reads various programs stored in the storage 22, loads the read programs to the RAM, performs various processes in accordance with the loaded programs, and performs centralized control of operation of the components of the console 2.

The storage 22 includes a nonvolatile memory, a hard disk and/or the like.

The storage 22 stores various programs that are executed by the CPU, parameters necessary for execution of the programs, and so forth.

In one or more embodiments, the storage 22 stores a fixed information table 221 in which default (standard) imaging conditions for each imaging region are stored.

Figures 3, 4:
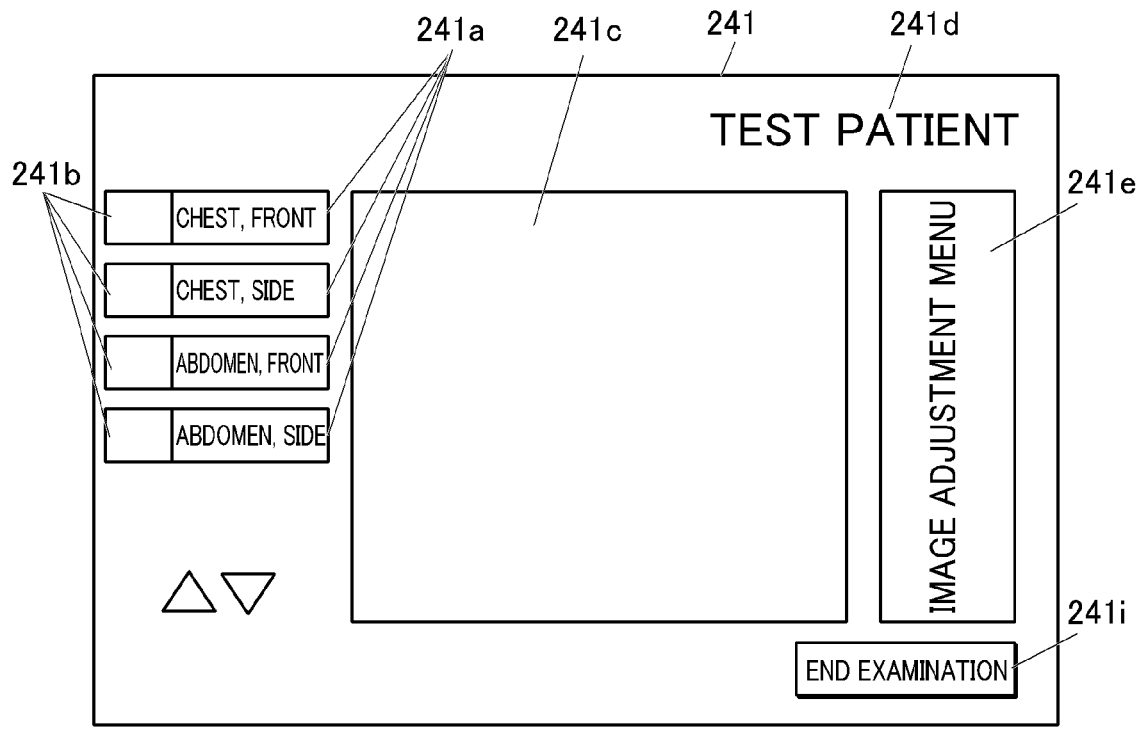
FIG. 3 shows an example of data storage in a fixed information table.
FIG. 4 shows an example of an examination screen.

FIG. 3 shows an example of the fixed information table 221. As shown in FIG. 3, in the fixed information table 221, each imaging region (e.g., "Head, Front", "Chest, Front", "Abdomen, Front", . . . ) is associated and stored with imaging conditions including irradiation conditions, examples of which include tube voltage, tube current, irradiation time, exposure dose, imaging distance, grid information, material(s) of a target and a filter of a radiation source, type of imaging stand, radiation field size, and type of radiation detector.

The fixed information table 221 is set by a technical expert at the time of installation of the console 2.

The storage 22 further stores examination order information received from an HIS, RIS or the like.

The storage 22 further stores each processed radiograph associated with, for example, an irradiation result flag indicating whether irradiation information has been applied (used) as processing parameters, processing parameters, patient information and examination information.

The communication unit 23 is configured by a communication module that may comprise a central processing unit (CPU) and transmitter/receiver, or the like. The communication unit 23 sends and receives various signals and various data to and from other apparatuses (detector 1, irradiation apparatus 3, etc.) connected thereto via the communication network N with wires or wirelessly.

The display 24 is configured by a liquid crystal display (LCD), a cathode ray tube (CRT) or the like. The display 24 displays various screens in accordance with image signals received from the controller 21.

The operation unit 25 includes a keyboard (cursor keys, numeric input keys, various function keys, etc.), a pointing device (mouse, etc.) and/or a touchscreen overlaid on the surface of the display 24. The operation unit 25 outputs, to the controller 21, control signals corresponding to operations made by a user.

The console 2 may not include the display 24 and/or the operation unit 25, and may receive control signals from an input apparatus provided separately from the console 2 and/or output image signals to a display apparatus (monitor) provided separately from the console 2 through the communication unit 23 or the like, for example.

[2-2. Operation of Console]

The controller 21 of the console 2 configured as described above operates as follows.

For example, when receiving examination order information from a not-shown HIS, RIS or the like through the communication unit 23, the controller 21 stores the received examination order information in the storage 22 and also displays the received examination order information in a not-shown examination list screen on the display 24. The examination order information includes an examination ID, an examination date, patient information, and imaging information (imaging region, imaging direction, posture, etc.) on each imaging included in the examination. When examination order information about an examination to be performed is selected from the examination list screen, the controller 21 causes the display 24 to display an examination screen 241.

FIG. 4 shows an example of the examination screen 241. As shown in FIG. 4, the examination screen 241 includes imaging condition buttons 241a, thumbnail display areas 241b, an image display area 241c, a patient information display area 241d, an image adjustment menu area 241e and an examination end button 241i.

The imaging condition buttons 241a are buttons each corresponding to each imaging included in examination order information, and are for setting imaging conditions (irradiation conditions and image reading conditions) for each imaging in the irradiation apparatus 3 and the detector 1. On the imaging condition buttons 241a, in order to distinguish imagings included in examination order information, imaging regions or the like of the respective imagings are displayed, for example.

The thumbnail display areas 241b are each an area where a thumbnail image of a radiograph obtained by radiography performed in response to a press on its adjacent imaging condition button 241a is displayed.

The image display area 241c is an area where a radiograph obtained by radiography is displayed.

The patient information display area 241d is an area where patient information on a patient (examinee) as an examination target is displayed.

The image adjustment menu area 241e is an area where an image adjustment menu for the radiograph displayed in the image display area 241c is displayed.

The examination end button 241i is a button for the operator (user) to make an instruction to end an examination.

The operator presses one of the imaging condition buttons 241a on the examination screen 241 for radiography (imaging) to be performed next, and prepares for imaging.

When the operator presses one of the imaging condition buttons 241a on the examination screen 241 by operating the operation unit 25, the controller 21 reads imaging conditions corresponding to the pressed imaging condition button 241a from the fixed information table 221 in the storage 22, and sends, of the fixed information, irradiation conditions (e.g., tube voltage, tube current, irradiation time, exposure dose, imaging distance, grid information, material of target and filter of radiation source, type of imaging stand, radiation field size, type of radiation detector, etc.) to the generator 31 of the irradiation apparatus 3 and image reading conditions to the detector 1, through the communication unit 23.

The generator 31 of the irradiation apparatus 3 sets the irradiation conditions received from the console 2 as irradiation conditions for radiography to be performed next. The detector 1 sets the image reading conditions received from the console 2 as image reading conditions for radiography to be performed next.

The operator places a subject S between the radiation source 33 and the detector 1 and performs positioning. Depending on the physique or the like of the subject S, if necessary, the operator inputs a change(s) with respect to the irradiation condition(s) by using the console panel connected to the generator 31 of the irradiation apparatus 3. When receiving the input of the change with respect to the irradiation condition(s), the generator 31 changes the setting(s) of the irradiation condition(s) in accordance with the input.

When finishing preparations for imaging, the operator operates the irradiation instructing switch 32. When the irradiation instructing switch 32 is operated, the generator 31 of the irradiation apparatus 3 causes the radiation source 33 to irradiate the subject S on the set irradiation conditions, and sends the irradiation information, which is irradiation conditions used in irradiation at the time of imaging, to the console 2. The irradiation information sent to the console 2 includes at least one of, for example, the tube voltage, the tube current, the irradiation time, the exposure dose, the imaging distance, the grid information, the material(s) of the target and the filter of the radiation source, the type of imaging stand, the radiation field size and the type of radiation detector at the time of imaging.

In sync with the irradiation apparatus 3, the detector 1 accumulates and reads the radiation with which the detector 1 is irradiated, and generates and then sends image data of a radiograph to the console 2.

In the console 2, when receiving the radiograph from the detector 1 through the communication unit 23, the controller 21 performs image processing on the radiograph and causes the display 24 to display the radiograph in the image display area 241c and one of the thumbnail display areas 241b on the examination screen 241.

More specifically, the controller 21 generates a wipe image, a preview image and a main image in this order from the received radiograph and causes the display 24 to display each generated image in the image display area 241c as soon as it is generated. The main image is an image generated by performing predetermined image processing, such as scattered radiation correction, gradation processing and/or frequency processing, on a radiograph without pixel thinning, and is displayed for diagnosis as an imaging result of the radiograph. The preview image is an image generated by performing, on a radiograph, simpler image processing than that for the main image, and is displayed before the main image is displayed. The wipe image is an image generated by performing, on a radiograph, simpler image processing than that for the preview image or no image processing, and is displayed before the preview image is displayed.

In one or more embodiments, the controller 21 generates the main image by performing image processing, such as scattered radiation correction, gradation processing and/or frequency processing, on the preview image. That is, scattered radiation correction is started after generation of the preview image, almost at the display timing of the preview image.

In scattered radiation correction, of the irradiation information, at least the tube voltage, the exposure dose and the imaging distance are used as processing parameters. Other pieces/types of information included in the irradiation information may be used as processing parameters. In the storage 22, the fixed information table 221 is stored. As a conventional method, scattered radiation correction is performed with irradiation conditions of fixed information sent to an irradiation apparatus as processing parameters. However, in the case where fixed information is used, if an irradiation condition is changed at an irradiation apparatus and imaging is performed, scattered radiation correction cannot be performed accurately and needs to be performed again, which is troublesome. It is conceivable that if an irradiation condition is changed at an irradiation apparatus and imaging is performed, an operator inputs the irradiation information accordingly, and scattered radiation correction is performed. However, it is troublesome and may cause incorrect input.

Meanwhile, irradiation apparatuses that send, after exposure, the irradiation information to a radiography control apparatus(es) require different lengths of time to send the irradiation information to the radiography control apparatus. Hence, if a radiography control apparatus always waits to perform scattered radiation correction until it receives the irradiation information, the start timing of scattered radiation correction may be delayed, which results in requirement of a long time to display an image (main image).

Figure 5:
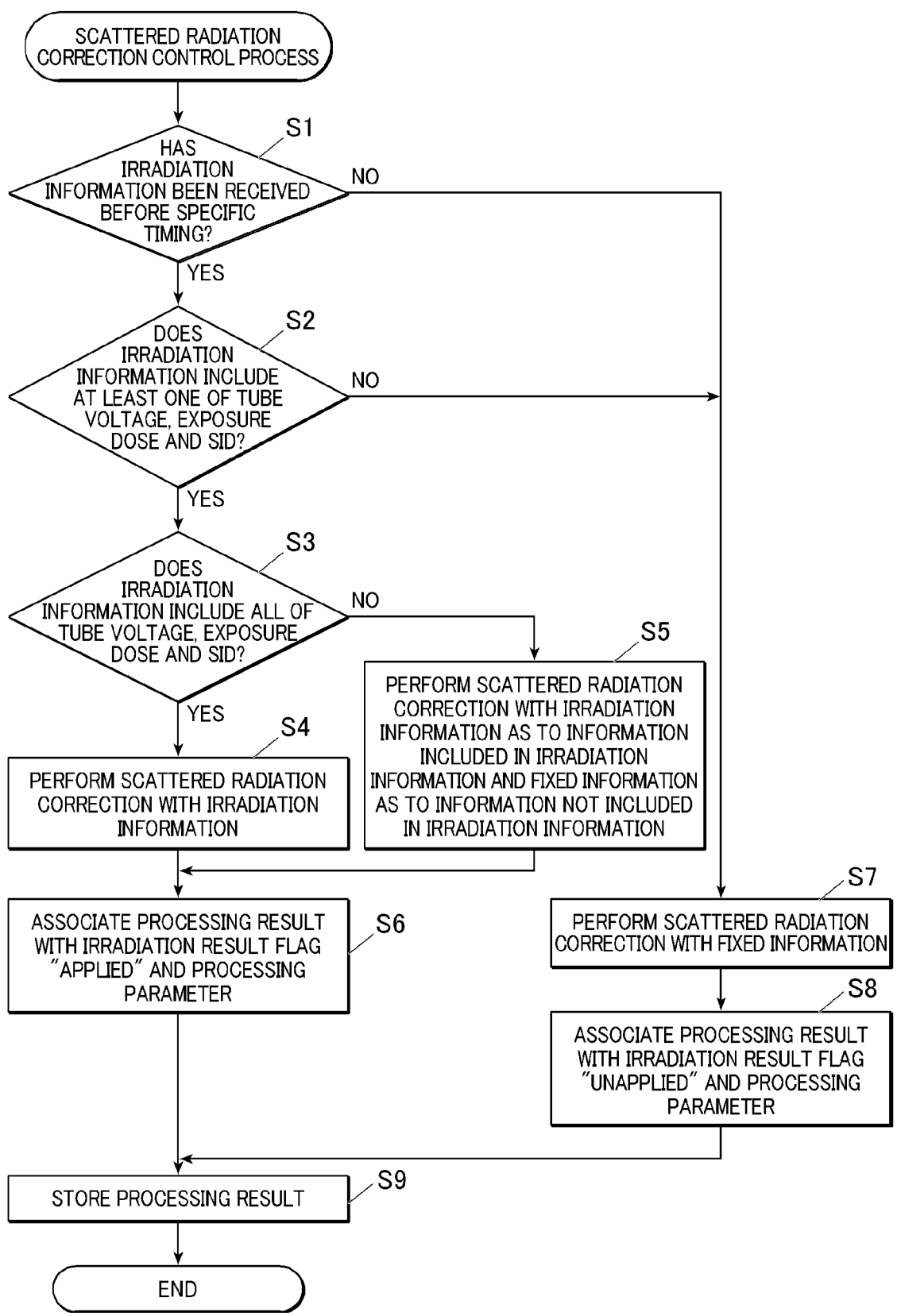
FIG. 5 is a flowchart of a scattered radiation correction control process that is performed by a controller shown in FIG. 2.

In order to deal with this, in the console 2 of one or more embodiments, the controller 21 performs, in cooperation with a program stored in the storage 22, a scattered radiation correction control process shown in FIG. 5, for example, at the timing when the controller 21 is about to perform scattered radiation correction on a radiograph. In this process, if the communication unit 23 receives (obtains) the irradiation information (information about irradiation with radiation (emission of radiation) at the time of imaging of the radiograph) from the irradiation apparatus 3 before a specific timing, the controller 21 performs scattered radiation correction on the basis of the obtained irradiation information, whereas if the communication unit 23 does not receive (obtain) the irradiation information from the irradiation apparatus 3 before the specific timing, the controller 21 performs scattered radiation correction on the basis of the fixed information stored in advance.

In one or more embodiments, the specific timing is timing at which a preview image of a radiograph is displayed. This is because if the irradiation information is obtained before the timing at which a preview image of a radiograph is displayed, a main image can be generated by accurate scattered radiation correction based on the irradiation information and can be displayed with no delay from the original timing at which the main image is supposed to be displayed. The specific timing may be timing at which a process to display a preview image of a radiograph is started, which is almost the same as the timing at which a preview image of a radiograph is displayed.

Hereinafter, the scattered radiation correction control process will be described with reference to FIG. 5.

First, the controller 21 determines whether it has received (obtained), through the communication unit 23, the irradiation information from the irradiation apparatus 3 before the specific timing, namely, the timing at which a preview image of a received radiograph from the detector 1 is displayed (Step S1).

If the controller 21 determines that it has received (obtained), through the communication unit 23, the irradiation information from the irradiation apparatus 3 before the specific timing (Step S1; YES), the controller 21 determines whether the received irradiation information includes at least one of the information on the tube voltage, the information on the exposure dose and the information on the imaging distance (Step S2).

Since "exposure dose=tube current×irradiation time", the tube current and the irradiation time may be used in Step S2 instead of the exposure dose.

If the controller 21 determines that the received irradiation information includes at least one of the information on the tube voltage, the information on the exposure dose and the information on the imaging distance (Step S2; YES), the controller 21 determines whether the received irradiation information includes all of the information on the tube voltage, the information on the exposure dose and the information on the imaging distance (Step S3).

As described above with respect to Step S2, since "exposure dose=tube current×irradiation time", the tube current and the irradiation time may be used in Step S3 instead of the exposure dose.

If the controller 21 determines that the received irradiation information includes all of the information on the tube voltage, the information on the exposure dose and the information on the imaging distance (Step S3; YES), the controller 21 performs scattered radiation correction on the received radiograph by using the received irradiation information as processing parameters (Step S4), and then proceeds to Step S6.

In one or more embodiments, scattered radiation correction is performed on the preview image generated from the radiograph.

If the controller 21 determines that the received irradiation information includes not all (does not include at least one) of the information on the tube voltage, the information on the exposure dose and the information on the imaging distance (Step S3; NO), the controller 21 performs scattered radiation correction on the radiograph by using, as to pieces/types of information included in the received irradiation information, pieces of the irradiation information as processing parameters, and as to pieces/types of information not included in the received irradiation information, pieces of the fixed information as processing parameters, the fixed information having been sent to the irradiation apparatus 3 as irradiation conditions for the radiograph (Step S5), and then proceeds to Step S6. As to a piece(s) of information not included in the received irradiation information but obtainable by calculation with piece(s) of information included in the received irradiation information, a value obtained by the calculation may be used as a processing parameter.

As a method for scattered radiation correction, well-known methods disclosed, for example, in JP 2019-126524 A, JP 2019-129988 A and so forth are usable. For example, there is a method of estimating the body thickness of a subject S on the basis of the tube voltage, the exposure dose and the imaging distance, estimating a scattered radiation component of each pixel of a radiograph on the basis of the estimated body thickness, and removing (subtracting) the estimated scattered radiation component from the radiograph. Scattered radiation correction may be performed with another piece(s) of information included in the irradiation information, such as the grid information.

In Step S5, before performing scattered radiation correction, the controller 21 performs a consistency check about the received irradiation information. Since the exposure dose (tube current×irradiation time) is used as a processing parameter in scattered radiation correction, if the received irradiation information employs a system of specifying irradiation conditions by three values of the tube voltage, the tube current and the irradiation time (three-point system), the controller 21 converts it into information that employs a system of specifying irradiation conditions by two values of the tube voltage and the exposure dose (two-point system), for example. This makes it possible to use, as processing parameters, the irradiation information received from the irradiation apparatus 3 that sends irradiation conditions by the three-point system.

In Step S6, the controller 21 associates the radiograph having undergone scattered radiation correction (processing result) with an irradiation result flag "applied" indicating that the irradiation information has been applied (used) as processing parameters (Step S6), stores the processing result associated with the irradiation result flag, used processing parameters, patient information, examination information and so forth in the storage 22 (Step S9), and then ends the scattered radiation correction control process.

On the other hand, if the controller 21 determines in Step S1 that it has not received (obtained), through the communication unit 23, the irradiation information from the irradiation apparatus 3 before the specific timing, namely, the timing at which a preview image of a received radiograph from the detector 1 is displayed (Step S1; NO), or determines in Step S2 that the received irradiation information does not include any of the information on the tube voltage, the information on the exposure dose and the information on the imaging distance (Step S2; NO), the controller 21 performs scattered radiation correction on the radiograph by using the fixed information as processing parameters, the fixed information having been sent to the irradiation apparatus 3 as irradiation conditions for the radiograph (Step S7).

Then, the controller 21 associates the radiograph having undergone scattered radiation correction (processing result) with an irradiation result flag "unapplied" indicating that the irradiation information has not been applied (used) (Step S8), stores the processing result associated with the irradiation result flag, used processing parameters, patient information, examination information and so forth in the storage 22 (Step S9), and then ends the scattered radiation correction control process.

Thus, in the scattered radiation correction control process shown in FIG. 5, if the communication unit 23 receives (obtains) the irradiation information from the irradiation apparatus 3 before the specific timing, for example, the timing at which a preview image of a radiograph is displayed, the controller 21 performs control to perform scattered radiation correction based on the obtained irradiation information. Receiving the irradiation information from the irradiation apparatus 3 before the specific timing makes the following possible: to perform accurate scattered radiation correction based on the irradiation conditions actually used for imaging without delay in displaying an image (main image); to save time and effort of the operator to perform reprocessing (i.e., perform scattered radiation correction again); to save time and effort of the operator to input the irradiation information every time a change(s) is made to the irradiation condition(s) at the time of radiography, and accordingly prevent incorrect input.

On the other hand, if the communication unit 23 does not receive (obtain) the irradiation information from the irradiation apparatus 3 before the specific timing, for example, the timing at which a preview image of a received radiograph is displayed, the controller 21 performs control to perform scattered radiation correction based on the fixed information stored in advance. This can prevent the start timing of scattered radiation correction from being delayed, and accordingly prevent a long time from being required to display an image (main image).

That is, the scattered radiation correction control process shown in FIG. 5 does not cause delay in displaying an image (main image), does not give the operator trouble of performing reprocessing or inputting the irradiation information, and can improve accuracy of image processing.

Further, since the console 2 can obtain the irradiation information from the irradiation apparatus 3, unlike conventional cases, at the time of installation of the irradiation apparatus 3, it is unnecessary to set detailed imaging condition keys (fixed information of irradiation conditions or the like for each imaging region) in the console 2. This can reduce steps that a technical expert needs to take.

After the scattered radiation correction control process, the controller 21 performs other image processing that has not been performed on the radiograph, thereby generating a main image, and causes the display 24 to display the main image in the image display area 241c on the displayed examination screen 241 and also display a thumbnail image of the main image in its corresponding thumbnail display area 241b on the displayed examination screen 241.

Figure 6:
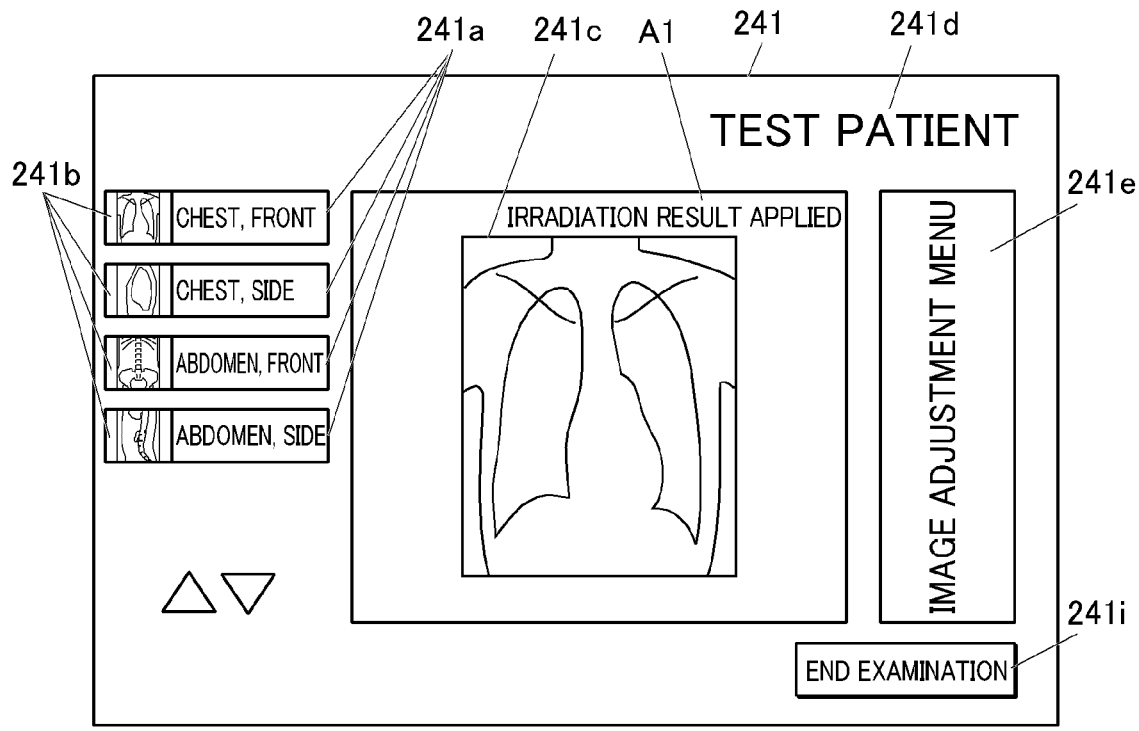
FIG. 6 shows an example in which a notification indicating whether irradiation information has been applied is displayed near a taken image as an overlay.
Figure 7:
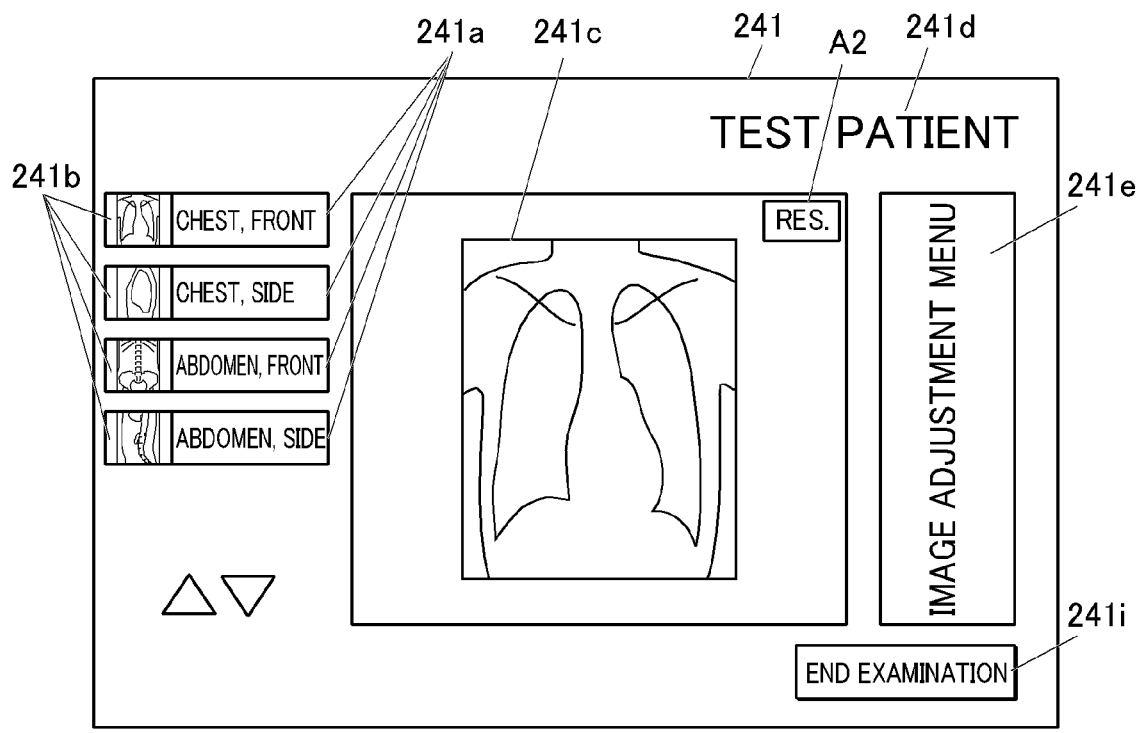
FIG. 7 shows another example in which the notification indicating whether the irradiation information has been applied is displayed near the taken image as an icon.

At the time, the controller 21 notifies the operator (user) about whether the irradiation information has been applied to (used in) scattered radiation correction. For example, as shown in FIG. 6, a notification indicating whether the irradiation information (irradiation result) has been applied may be displayed as an overlay A1 on or near a taken image or a thumbnail image, or as shown in FIG. 7, may be displayed as an icon A2. The A1 in FIG. 6 and the A2 in FIG. 7 are examples of notification that the irradiation information has been applied. The notification may not be displayed, but may be made by audio signal, optical signal or the like.

This allows the operator to know whether the irradiation information has been applied as processing parameters to scattered radiation correction that a displayed radiograph has undergone.

<Modifications>

Hereinafter, modifications of one or more embodiments will be described.

In one or more embodiments, the irradiation information is used as processing parameters in scattered radiation correction, but may be used as processing parameters in image processing other than scattered radiation correction, for example, in at least one of edge enhancement, structure enhancement, noise suppression, incident surface dose processing, body thickness estimation, frequency processing and grid moiré removal.

For example, as described above, the body thickness of a subject can be estimated on the basis of the tube voltage, the exposure dose and the imaging distance included in the irradiation information, and scattered radiation correction and incident surface dose calculation (process to calculate a dose value on the body surface) can be performed with the estimated body thickness (body thickness estimate). Further, body thickness estimation to output the body thickness estimate itself enables statistical processing of the exposed dose for each physique type of patients.

Further, the irradiation information, such as the tube voltage, the exposure dose and the imaging distance, can be used not only for body thickness estimation, but also as rough standards to measure S/N and graininess of radiographs. On the basis of the S/N and/or the graininess of a radiograph(s), intensity of frequency processing, noise suppression or the like can be changed. Thus, the irradiation information is useful for optimization of image processing.

Further, the irradiation information may include the grid information. The grid information can be used to perform scattered radiation correction suitable for a grid, and also can be used in grid moiré removal or the like.

When the aforementioned image processing other than scattered radiation correction is about to be performed with the irradiation information as processing parameters, a control process similar to the scattered radiation correction control process shown in FIG. 5 (i.e., the control process same as the scattered radiation correction control process except that scattered radiation correction is replaced by other image processing) may be performed.

Further, in one or more embodiments, the specific timing is the timing at which a preview image of a radiograph is displayed, and if the communication unit 23 receives the irradiation information before the specific timing, the controller 21 performs image processing with the received irradiation information, whereas if the communication unit 23 does not receive the irradiation information before the specific timing, the controller 21 performs image processing with the fixed information stored in advance in the storage 22, but the specific timing is not limited thereto. For example, the specific timing may be timing at which a wipe image, a preview image or a main image of a radiograph is displayed on the display 24, timing at which a process to display a wipe image, a preview image or a main image of a radiograph on the display 24 is started, timing at which image processing other than the image processing to which the irradiation information is applied is performed, timing at which an examination is ended (timing at which an examination related to the obtained irradiation information is ended, such as timing at which the examination end button 241i is pressed), or the like.

For example, in the case where incident surface dose calculation is performed as image processing, since it does not affect images, the timing at which an examination is ended can be specified as the specific timing. In the case where frequency processing is performed as image processing, the timing at which its preceding image processing (e.g., grid moiré removal) is performed can be specified as the specific timing.

Further, in the console 2, whether to perform image processing, such as scattered radiation correction, with the irradiation information as processing parameters or perform the image processing with the fixed information stored in advance in the storage 22 as processing parameters is settable by the user (operator) with the operation unit 25.

Figure 8:
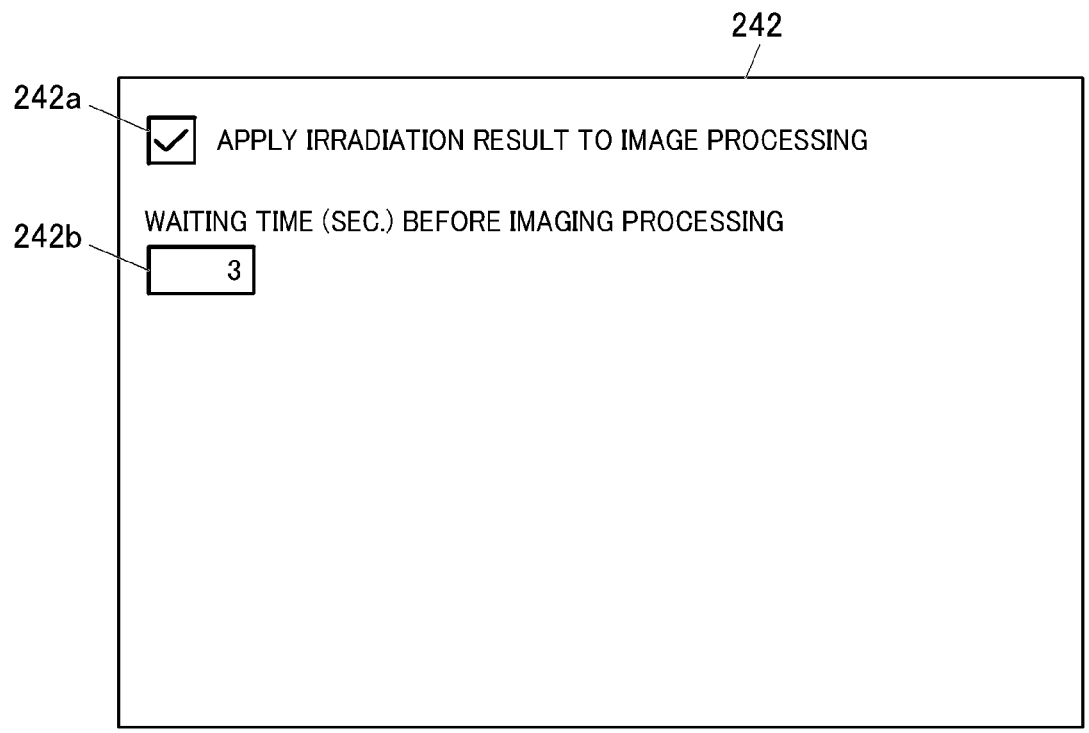
FIG. 8 shows an example of a setting screen.

For example, the controller 21 causes the display 24 to display a setting screen 242 as shown in FIG. 8 in response to a setting screen display instructing operation made with the operation unit 25, and if a check mark is input in a check box 242a for "Apply Irradiation Result to Image Processing", the controller 21 stores, in the storage 22, setting information indicating that image processing is performed with the irradiation information as processing parameters, whereas if a check mark is not input in the check box 242a or removed from the check box 242a, the controller 21 stores, in the storage 22, setting information indicating that image processing is performed with the fixed information as processing parameters. Then, when the controller 21 is about to perform predetermined image processing, such as scattered radiation correction, if it is set that the predetermined image processing is performed with the irradiation information as processing parameters, the controller 21 performs the control process same as or similar to the scattered radiation correction control process shown in FIG. 5, whereas if it is set that the predetermined image processing is performed with the fixed information as processing parameters, the controller 21 performs the predetermined image processing with the fixed information, no matter whether it receives (obtains) the irradiation information.

In the console 2, whether to perform image processing, such as scattered radiation correction, with the irradiation information as processing parameters or perform the image processing with the fixed information stored in advance in the storage 22 as processing parameters is settable by the user with the operation unit 25 for each imaging mode (e.g., plain imaging, long-length imaging, movie imaging) or for each imaging condition.

Further, in the scattered radiation correction control process shown in FIG. 5 (including the case where scattered radiation correction is replaced by other image processing), if the irradiation information is obtained after image processing with the fixed information stored in advance as processing parameters, the controller 21 may perform the image processing again (reprocessing) with the obtained irradiation information as processing parameters. After reprocessing, the controller 21 may replace the image displayed on the display 24 with the reprocessed image.

Figure 9:
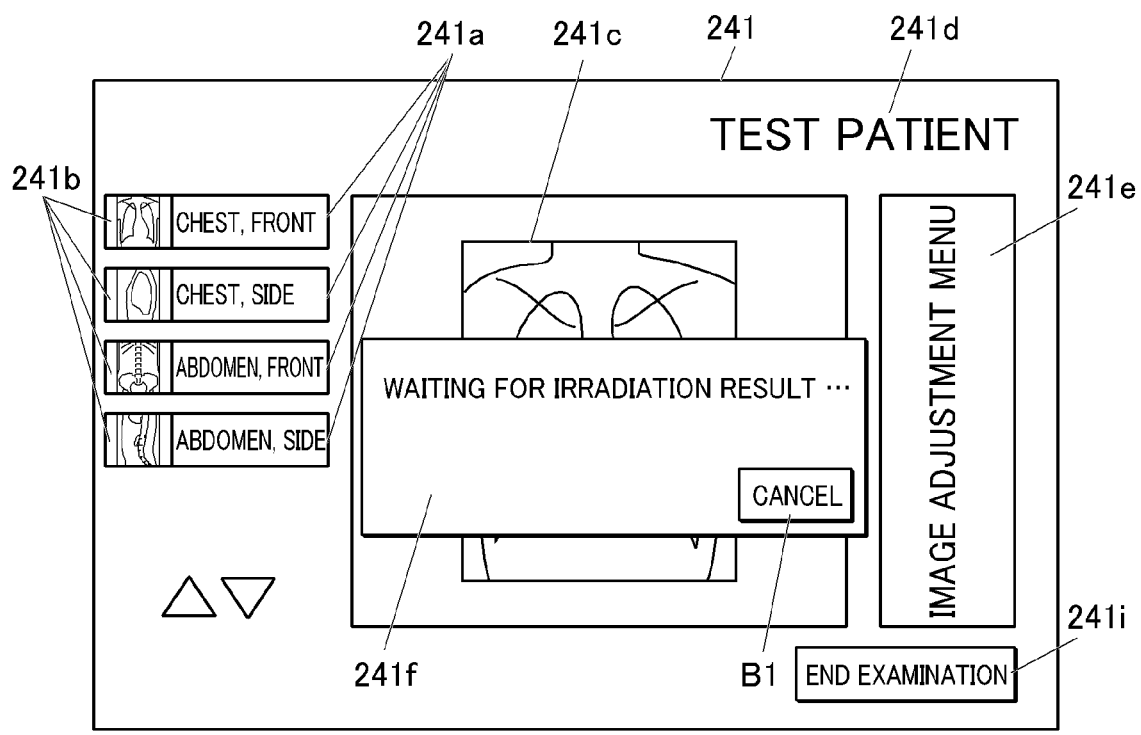
FIG. 9 shows a display example on a screen during waiting time for the irradiation information to be obtained.

Further, the controller 21 may wait to perform image processing until it obtains the irradiation information. During the waiting time, for example, as shown in FIG. 9, a dialog box 241f is displayed where a message notifying the user of waiting for irradiation information is displayed, and when the controller 21 obtains the irradiation information, the controller 21 may perform image processing on a radiograph with the obtained irradiation information as processing parameters. Further, as shown in FIG. 9, in the dialog box 241f, a cancel button B1 may be displayed, and when the cancel button B1 is pressed, the controller 21 may stop waiting and perform image processing on a radiograph with the fixed information as processing parameters. This makes it possible to perform image processing that suits the user's needs of image quality or processing speed, whichever is more important for the user.

Further, the controller 21 may set, in advance, a waiting time before image processing, and if the controller 21 obtains the irradiation information before the set waiting time elapses, the controller 21 performs image processing on a radiograph with the irradiation information as processing parameters, whereas if the controller 21 does not obtain the irradiation conditions at the time of imaging (i.e., irradiation information) before the set waiting time elapses, the controller 21 performs image processing on a radiograph with the fixed information as processing parameters. That is, the aforementioned specific timing may be the timing at which a preset waiting time elapses.

The waiting time may be changeable (i.e., the controller 21 may automatically set the waiting time) in accordance with specifications, image transfer time and/or the like of the connected irradiation apparatus 3 or the console 2 itself. Alternatively, a fixed time specified by the user may be set as the waiting time. For example, the controller 21 causes the display 24 to display the setting screen 242 as shown in FIG. 8 in response to a setting screen display instructing operation made with the operation unit 25, and if a waiting time is input in a waiting time input section 242b, the controller 21 stores the input waiting time in the storage 22 as setting information.

As the starting point of the waiting time, the following may be used: timing at which the console 2 receives an exposure-finished signal sent from the irradiation apparatus 3 after exposure with radiation (irradiation); timing at which the console 2 receives a radiograph from the detector 1; and other timing.

Further, if the controller 21 obtains the irradiation information after starting image processing with the fixed information as processing parameters or while waiting to perform image processing, the controller 21 may notify the user of having obtained the irradiation information.

Figure 10:
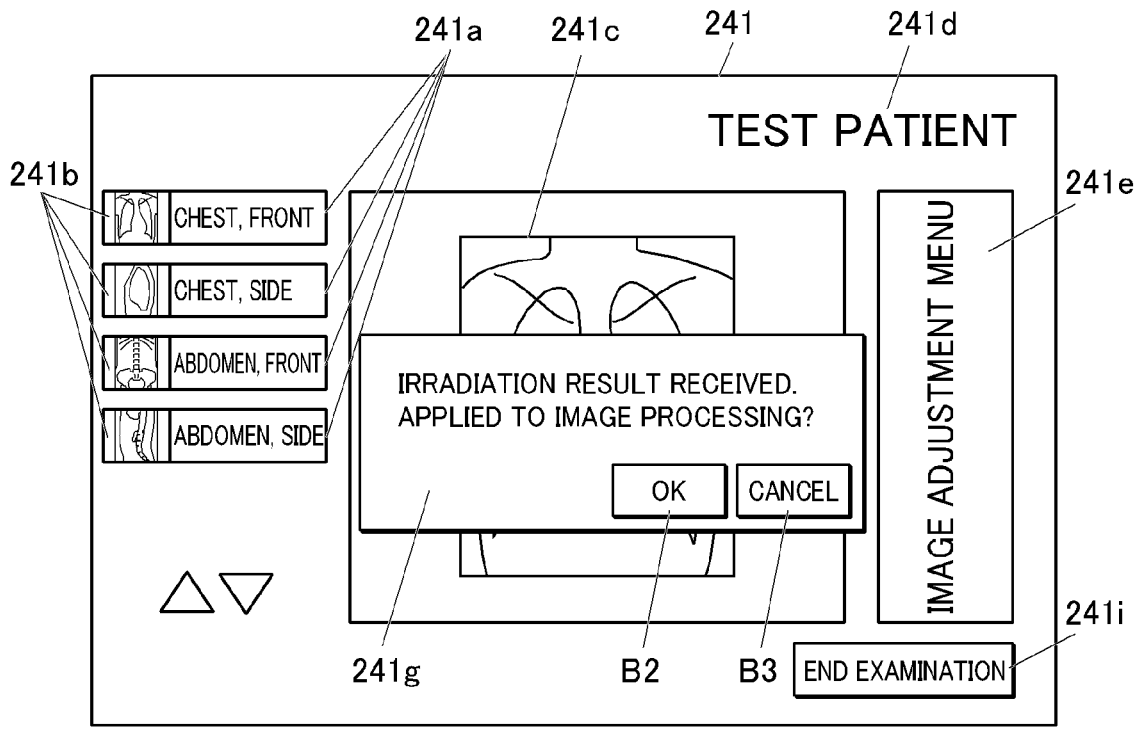
FIG. 10 shows a display example on the screen when the irradiation information was received after image processing with fixed information as processing parameters was started or while image processing is on hold.

For example, as shown in FIG. 10, the controller 21 causes the display 24 to display a message dialog box 241g where a message notifying the user of having received the irradiation information and asking the user whether to apply the received irradiation information to image processing, an OK button B2 and a cancel button B3 are displayed, and when the OK button B2 is operated by the user, performs image processing with the received irradiation information as processing parameters, and when the cancel button B3 is operated by the user, continues to perform image processing with the fixed information as processing parameters or wait to perform image processing.

Figure 11:
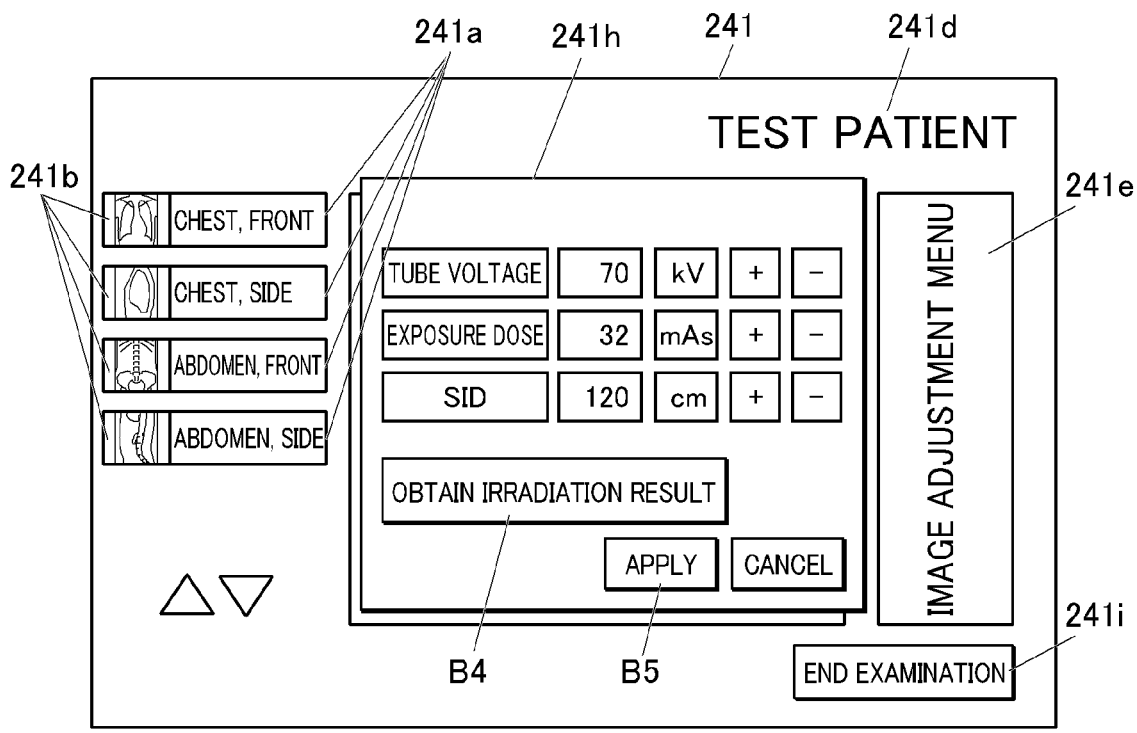
FIG. 11 shows a display example on the screen when the irradiation information was received after image processing with fixed information as processing parameters was started or while image processing is on hold, to obtain and apply the irradiation information as processing parameters.

Alternatively, the controller 21 performs control to output, by display or audio signal, a message notifying the user of having received the irradiation information, and causes the display 24 to display a re-apply dialog box 241h (shown in FIG. 11) where a fixed button (e.g., an irradiation result obtaining button B4) to make an instruction to obtain the irradiation information, an apply button B5 and so forth are displayed, and when the irradiation result obtaining button B4 and the apply button B5 are pressed, performs image processing with the received irradiation information as processing parameters.

Still alternatively, the controller 21 automatically performs image processing with the irradiation information as processing parameters as soon as it obtains the irradiation information.

If the controller 21 obtains the irradiation information piece by piece, the controller 21 waits to perform image processing until it obtains all or part of the irradiation information, the part being parameters necessary for image processing.

Further, even if the controller 21 obtains the irradiation information before the specific timing, the controller 21 may use the fixed information as processing parameters, depending on the type of image processing. The type(s) of image processing in which the fixed information is used may be settable in advance by the user with the operation unit 25.

Further, if the controller 21 cannot obtain the irradiation information owing to, for example, an error in communications between the console 2 and the irradiation apparatus 3 or an error in the irradiation apparatus 3 itself, the controller 21 notifies the user that application of the irradiation information to image processing has failed. As the notification, a message dialog box may be displayed on the examination screen 241 of the display 24, the message dialog box where "Application of Irradiation Result to Image Processing has Failed" or the like is displayed, or a similar message may be output by audio.

Further, if a radiograph is a failed image and re-imaging is necessary, the controller 21 may save the obtained irradiation information in the RAM or the storage 22, and perform image processing on a radiograph obtained by re-imaging with the saved irradiation information as processing parameters.

Further, if a copy/duplicate of a radiograph (copy source) is made, the controller 21 may save the irradiation information of the original radiograph in the copy (e.g., in its accessary information or the like, and perform image processing on the copy with the saved irradiation information as processing parameters.

Hence, if re-imaging or copying is performed with no change made to the irradiation conditions at the time of imaging of the original image, which is a failed image or a copy source, the controller 21 can perform image processing on an image obtained by re-imaging or copying without waiting to obtain the irradiation information of the image.

Further, if examination order information includes imaging of multiple imaging regions, the imaging regions are usually imaged in order of being requested (original order of imaging), but depending on the patient's condition, imaging efficiency or the like, the imaging regions may be imaged in a different order, and consequently become different image regions (image regions after change) as compared with those scheduled to be imaged in the original order of imaging. This change of the imaging regions may be registered later at the console 2. In such a case, if the controller 21 obtains the irradiation information before the specific timing, the controller 21 performs image processing (or reprocessing) on a radiograph of an image region after change with the irradiation information as processing parameters, whereas if the controller 21 does not obtain the irradiation information before the specific timing, the controller 21 performs image processing (or reprocessing) on the radiograph of the imaging region after change with the fixed information associated with the imaging region after change as processing parameters.

Further, if a radiograph obtained by previous imaging is associated and stored with the irradiation information, the controller 21 may overwrite, with the irradiation information, the fixed information in the fixed information table 221 for the imaging region same as that of the radiograph.

Further, in one or more embodiments, the irradiation apparatus 3 has the functions of an irradiation console, but a single console may have both the functions of the console 2 as the radiography control apparatus and the functions of the irradiation console.

Although the embodiments and its modifications have been described in the above, those described in the embodiments and the modifications are not limitations but some examples of the radiography control apparatus of the present disclosure.

For example, in the above, the computer-readable storage medium storing the programs of the present disclosure is a hard disk, a nonvolatile semiconductor memory or the like, but not limited thereto and may be a portable recording medium, such as a CD-ROM. Further, as a medium to provide data of the programs of the present disclosure via a communication line, a carrier wave can be used.

The detailed configurations and operations of the components of the radiography control apparatus can be appropriately changed within a range not departing from the scope of the present invention.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

What is claimed is:

1. A radiography control apparatus comprising:
a storage that stores an irradiation condition;
a communicator that sends, to an irradiation apparatus, the irradiation condition stored in the storage and that obtains, from the irradiation apparatus, an irradiation condition that has changed at the irradiation apparatus;
a hardware processor that:
upon determining that the communicator obtains the irradiation condition from the irradiation apparatus before a specific timing, executes image processing based on the changed irradiation condition obtained via the communicator from the irradiation apparatus; and
upon determining that the communicator does not obtain the irradiation condition from the irradiation apparatus before the specific timing, executes the image processing based on the stored irradiation condition in the storage.

2. The radiography control apparatus according to claim 1, wherein
the image processing is at least one of: scattered radiation correction; edge enhancement; structure enhancement; noise suppression; incident surface dose processing; body thickness estimation; frequency processing; and grid moiré removal.

3. The radiography control apparatus according to claim 1, further comprising:
a display, wherein
the specific timing is any one of:
a timing at which the hardware processor displays a wipe image, a preview image, or a main image on the display;
a timing at which the hardware processor starts a process to display the wipe image, the preview image, or the main image on the display;
a timing at which the hardware processor executes different image processing from the image processing; and
a timing at which the hardware processor ends an examination related to the stored irradiation condition.

4. The radiography control apparatus according to claim 1, further comprising:
a user interface that receives an operation to set whether to execute the image processing based on the changed irradiation condition obtained from the communicator or based on the stored irradiation condition in the storage.

5. The radiography control apparatus according to claim 1, wherein
the communicator obtains the changed irradiation condition at a time of imaging, and
the changed irradiation condition includes at least one of: an imaging distance; an exposure dose; a tube voltage; an irradiation time; a tube current; a material of a target and a filter of a radiation source; a type of an imaging stand; a radiation field size; grid information; and a type of a radiation detector.

6. The radiography control apparatus according to claim 1, wherein
the irradiation condition is changed with respect to the irradiation condition sent by the communicator, by using a console panel connected to the irradiation apparatus.

7. An image processing control method comprising:
storing, in a storage, an irradiation condition;
sending, to an irradiation apparatus, the stored irradiation condition in the storage;
obtaining, from the irradiation apparatus, an irradiation condition that has changed at the irradiation apparatus;
upon determining that the irradiation condition is obtained from the irradiation apparatus before a specific timing, executing image processing based on the changed irradiation condition obtained from the irradiation apparatus; and upon determining that the irradiation condition is not obtained from the irradiation apparatus before the specific timing, executing the image processing based on the stored irradiation condition in the storage.

8. A non-transitory computer-readable storage medium storing a program that causes a computer to:

store, in a storage, an irradiation condition;

send, to an irradiation apparatus, the stored irradiation condition in the storage;

obtain, from the irradiation apparatus, an irradiation condition that has changed at the irradiation apparatus;

upon determining that the irradiation condition is obtained from the irradiation apparatus before a specific timing, execute image processing based on the changed irradiation condition obtained from the irradiation apparatus; and upon determining that the irradiation condition is not obtained from the irradiation apparatus before the specific timing, execute the image processing based on the stored irradiation condition in the storage.

* * * * *